(12) United States Patent
Jo

(10) Patent No.: US 9,788,967 B2
(45) Date of Patent: Oct. 17, 2017

(54) INTERVERTEBRAL CAGE FOR SPINAL IMPLANT

(71) Applicant: Dae Jean Jo, Seoul (KR)

(72) Inventor: Dae Jean Jo, Seoul (KR)

( * ) Notice: Subject to any disclaimer, the term of this patent is extended or adjusted under 35 U.S.C. 154(b) by 0 days.

(21) Appl. No.: 14/807,996

(22) Filed: Jul. 24, 2015

(65) Prior Publication Data

US 2016/0151167 A1    Jun. 2, 2016

(30) Foreign Application Priority Data

Dec. 1, 2014  (KR) ......................... 10-2014-0169588

(51) Int. Cl.
*A61F 2/44* (2006.01)
*A61F 2/28* (2006.01)
*A61F 2/30* (2006.01)
*A61F 2/46* (2006.01)

(52) U.S. Cl.
CPC .... *A61F 2/4455* (2013.01); *A61F 2002/2835* (2013.01); *A61F 2002/30158* (2013.01); *A61F 2002/30364* (2013.01); *A61F 2002/30784* (2013.01); *A61F 2002/30841* (2013.01); *A61F 2002/4475* (2013.01); *A61F 2002/4629* (2013.01)

(58) Field of Classification Search
CPC ...................................... A61F 2/44–2002/4495
USPC ..................................... 623/17.16; 248/206.3
See application file for complete search history.

(56) References Cited

U.S. PATENT DOCUMENTS

| 4,863,477 | A | * | 9/1989 | Monson | A61F 2/441 623/17.12 |
| 5,071,437 | A | * | 12/1991 | Steffee | A61F 2/442 606/247 |
| 5,571,105 | A | * | 11/1996 | Gundolf | A61B 17/82 24/21 |
| 5,609,635 | A | * | 3/1997 | Michelson | A61F 2/30744 606/247 |
| 6,113,638 | A | * | 9/2000 | Williams | A61F 2/442 128/898 |
| 6,342,074 | B1 | * | 1/2002 | Simpson | A61F 2/4455 623/17.11 |

(Continued)

FOREIGN PATENT DOCUMENTS

KR    2003-0063309 A    7/2003
KR    10-0972397 B1    7/2010

(Continued)

OTHER PUBLICATIONS

Korean Intellectual Property Office, Notice of Allowance issued in counterpart KR 10-2014-0169588 dated Feb. 26, 2015.

*Primary Examiner* — Zade Coley
(74) *Attorney, Agent, or Firm* — KORUS Patent, LLC; Seong Il Jeong

(57) ABSTRACT

An intervertebral cage for spinal implants is provided. The intervertebral cage includes a front portion, a right lateral portion, a left lateral portion, a rear portion, a top portion and a bottom portion. A vertical dimension of the front portion is larger than a vertical dimension of the rear portion. A vertical dimension of the right portion is larger than a vertical dimension of the left portion. A vertical dimension of a connection between the left and rear portions is smaller than a vertical dimension of a connection between the right and front portions.

3 Claims, 12 Drawing Sheets

(56) References Cited

U.S. PATENT DOCUMENTS

| | | | | |
|---|---|---|---|---|
| 6,458,159 B1* | 10/2002 | Thalgott | A61F 2/4455 606/247 |
| 6,458,161 B1* | 10/2002 | Gibbs | A61F 2/30724 623/22.32 |
| 6,620,196 B1* | 9/2003 | Trieu | A61F 2/441 623/17.16 |
| 6,716,245 B2* | 4/2004 | Pasquet | A61F 2/4611 606/99 |
| 6,758,862 B2* | 7/2004 | Berry | A61F 2/4455 606/247 |
| 7,044,972 B2* | 5/2006 | Mathys, Jr. | A61F 2/4455 623/17.11 |
| 7,135,043 B2* | 11/2006 | Nakahara | A61F 2/4455 623/17.11 |
| 7,226,480 B2* | 6/2007 | Thalgott | A61F 2/4455 623/17.11 |
| 7,238,203 B2* | 7/2007 | Bagga | A61F 2/4455 623/17.11 |
| 7,361,193 B2* | 4/2008 | Frey | A61B 17/025 623/17.11 |
| 7,591,852 B2* | 9/2009 | Prosser | A61F 2/4465 623/17.11 |
| 7,846,207 B2* | 12/2010 | Lechmann | A61B 17/86 623/17.11 |
| 7,875,080 B2* | 1/2011 | Puno | A61F 2/30771 623/17.16 |
| 7,918,891 B1* | 4/2011 | Curran | A61F 2/447 623/17.16 |
| 8,157,865 B2* | 4/2012 | Hochschuler | A61F 2/4455 606/279 |
| 8,216,312 B2* | 7/2012 | Gray | A61B 17/7059 606/249 |
| 8,349,015 B2* | 1/2013 | Bae | A61B 17/846 623/17.16 |
| 8,419,797 B2* | 4/2013 | Biedermann | A61B 17/8047 606/289 |
| 8,506,636 B2* | 8/2013 | Dye | A61F 2/4465 623/17.11 |
| 8,540,769 B2* | 9/2013 | Janowski | A61F 2/4455 623/17.11 |
| 8,900,309 B2* | 12/2014 | James | A61F 2/4455 623/17.16 |
| 8,932,360 B2* | 1/2015 | Womble | A61B 17/0642 623/17.16 |
| 2002/0156528 A1* | 10/2002 | Gau | A61F 2/442 623/17.11 |
| 2003/0109928 A1* | 6/2003 | Pasquet | A61F 2/4455 623/17.11 |
| 2005/0049590 A1* | 3/2005 | Alleyne | A61F 2/442 623/17.11 |
| 2005/0203627 A1* | 9/2005 | Choksey | A61F 2/44 623/17.15 |
| 2006/0106381 A1* | 5/2006 | Ferree | A61F 2/4455 606/248 |
| 2006/0235531 A1* | 10/2006 | Buettner-Janz | A61F 2/4425 623/17.15 |
| 2010/0152853 A1* | 6/2010 | Kirschman | A61F 2/447 623/17.11 |
| 2012/0130432 A1* | 5/2012 | Ferree | A61F 2/4455 606/279 |

FOREIGN PATENT DOCUMENTS

| | | |
|---|---|---|
| KR | 10-0980451 B1 | 9/2010 |
| KR | 10-2013-0032575 A | 4/2013 |

* cited by examiner

INTERVERTEBRAL CAGE FOR SPINAL IMPLANT

CROSS-REFERENCE TO RELATED APPLICATION(S)

This application claims the benefit of Korean Patent Application No. 10-2014-0169588, filed on Dec. 1, 2014, which is hereby incorporated by reference herein in its entirety.

BACKGROUND

1. Technical Field

The present invention relates generally to an intervertebral cage for spinal implants and, more particularly, to an intervertebral cage for spinal implants configured such that the cage can be mounted freely in front, lateral side or inclined direction relative to the vertebrae, wherein the front side has a trapezium face, the right lateral side and left lateral side are configured such that a left vertical line and a right vertical line are lengthened, and the length of the right vertical line of the left lateral is a shorter than that of the left vertical line of the right lateral, and the front side and the right lateral include a plurality of holes to which a tool is temporarily coupled.

2. Description of the Related Art

In general, an intervertebral cage for spinal implants is inserted into a disc-removed intervertebral gap and is an artificial prostheses apparatus for restoring and maintaining an interval between two vertebrae. Such an intervertebral cage for the spinal implants is currently formed in various shapes and is widely used to surge the vertebrae.

However, in order to replace a spinal disc due to abrasion of the disc, a frontal and lateral cage that is inserted at the position of the worn spinal disc has been currently developed and is used for the spinal disc operation.

FIGS. 1 to 3 are a perspective view, a plan view and a side view showing a conventional intervertebral cage, respectively.

As shown in FIGS. 1 to 3, a conventional intervertebral cage 10 has a width (horizontal length in the figures) and a height corresponding to the width and height of a disc (36 in FIG. 4) positioned between vertebral bodies (32 and 34 in FIG. 4 and 34 in FIG. 5); a through hole 14 having a width vertically elongated is provided at the center of the intervertebral cage; small circular holes 17 and 18 are formed at the central portion of the front and back of the cage, respectively, so that these holes communicate with the through hole 14; a plurality of teeth 15, 16 and 19 are formed in an upper and bottom sides of the cage that are contacted with and adjacent to a lateral part of the through hole 14; and a groove 13 is formed at both laterals of a right lateral 11 of the cage.

The method of using the above-mentioned conventional lateral cage 10 will be described as follows:

Before the lateral cage 10 is inserted into a damaged disc of a patient whose a spinal disc is worn or damaged, granulated bone chips are mixed with the patient's bone marrow or blood and then inserted into the through hole 14 of the lateral cage 10 and hardened. Next, as shown in FIG. 4, the groove 13 formed at both sides of the right lateral 11 of the lateral cage 10 is picked up with pincers (20 in FIG. 4) and the lateral cage is inserted into the position of the damaged disc 36 between the bodies 32 and 34 of the spine through an incised lateral side corresponding to the damaged disc of patients. At this time, the lateral cage may be inserted by knocking on the pincers using a kind of hammer.

FIG. 5 is a plan view showing the inserted lateral cage. The conventional lateral cage has a problem as follows:

First of all, a frontal cage may be used only in a frontal direction and a lateral cage may be used only in a lateral direction. The lateral cage cannot be replaced with the frontal cage during actual surgery, and if the frontal cage instead of the lateral cage is inserted by force in the case wherein there is a narrow space between the discs, it may cause damage to a vertebral disc. This results in complications such as non-union of the spine during use.

Also, since the height of the tip of a left lateral 12 of the lateral cage 10 that is first inserted into patient's spine during surgery, is formed to be substantially the same as that of the other part, a great amount of power must be applied between the vertebrae in the case wherein there is a narrow space between the discs and this may cause the vertebra board to be damaged. Further, if a great amount of power is applied, a bone chip 40 (FIG. 5) may be lost before it is placed between the vertebrae and so complications such as non-union of the spine may be caused while the vertebral surgery time is elapsed.

Also, FIGS. 6 and 7 show an intervertebral cage of the prior art (Japanese un-examined Laid-open publication No. 9-503416; Japanese patent application No. 199-511847). An intervertebral cage 50 comprises a pair of left and right semicircular lateral spacers 51A and 51B, a front and a rear central spacers 53A and 53B integrally fixed to each other by left and right fixing screws 55. The intervertebral cage 50 is inserted between an upper intervertebral body 59U and a lower intervertebral body 59L after removal of a disc. A cavity 57 is formed by the central spacers 53A and 53B and the lateral spacers 51A and 51B.

The intervertebral cage 50 of the prior art has problems in that 1) the cage consists of a large number of components and has a complex structure and 2) the cage cannot secure enough between the vertebrae after the insertion between the vertebral bodies, because they do not have a projection for preventing a loss of the intervertebral cage. Further, the intervertebral cage 50 of the prior art is inserted between the upper body and the lower body from a frontal direction, but it is not inserted from the vertical direction to an inclined front side. Accordingly, an improved intervertebral cage is required. That is, the intervertebral cage of the prior art has separate configurations for cases in which there is a front cage, a lateral cage, or an inclined cage, etc. and other configurations of the auxiliary apparatuses are also used as the other components.

SUMMARY

Aspects of the present invention are intended to address at least the above-mentioned problems and/or disadvantages and to provide at least the advantages described below. Accordingly, an object of the present invention is to provide an intervertebral cage that may be inserted into vertebral spines in the front, lateral and inclined direction relative to the vertebrae in order to be able to freely select the insertion direction of the intervertebral cage in accordance with the needs of a user. Ultimately, the present invention is intended to reduce the costs of consumable medical supplies.

In accordance with an aspect of the present invention, an intervertebral cage for spinal implants is provided. The intervertebral cage comprises: a front side 10; a right lateral 20; a left lateral 30; a rear side 40; a plane 50; and a bottom 60 configured to have a shape of "日" (Chinese character) in which vertical holes are formed on both sides, wherein the front side 10 has a trapezium face on the left side and a rectangle face on the right side, the right lateral 20 is disposed on the right of the front side and comprises a lengthened left vertical line, a sloping upper line and lower line and a shortened right vertical line, the intervertebral cage left lateral 30 is disposed on the left of the front side of the intervertebral cage and comprises a lengthened right vertical line, a sloping upper line and lower line and a shortened left vertical line in the form of trapezium, the right lateral vertical line disposed on the left side being shorter than the left vertical line disposed on the right side, the rear side 40 is disposed on the back of the front side and has a trapezium face on the left side and a rectangle face on the right side, and the plane 50 and the bottom 60 are disposed on the upper and lower parts of the front side and further comprise a slippage preventing means for improving the contact of vertebrae.

A plurality of striking-auxiliary holes 1 for temporarily coupling and striking a tool are formed along the front side 10 and the right lateral 20 in order to allow the intervertebral cage to be inserted between the vertebrae.

The slippage preventing means 70 may comprise an embossing structure 70a having a concave portion and a convex portion, the concave and the convex portions being sequentially formed, or a vacuum compressed structure 70b having a truncated cone in which the concave portion is formed on the inside so as to enable vacuum compression.

The slippage preventing means 70 may further comprise a hooked structure 70c to be not easily moved backward when the intervertebral cage is coupled between the vertebrae.

The hooked structure 70c may comprise a fixing portion 70d and a movable chain hook 70e, the chain hook 70e being installed to be self-rotated.

The slippage preventing means 70 may comprise an embossing structure 70f having a concave portion and a convex portion, the concave and the convex portions being sequentially formed, and the embossing structure 70f being formed on an inner lateral 10a of the intervertebral cage.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Hereinafter, the method of operation of a preferred embodiment of the present invention will be described with reference to the accompanying drawings and the description. However, the drawings and the description only illustrate a preferred method of implementation from among several such methods for the purpose of effectively describing the features of the present invention, and the present invention is not limited only to these drawings and description.

Furthermore, in describing the present invention, if known functions and constructions are deemed to make the gist of the invention unnecessarily complex, the detailed description thereof will be omitted.

Further, the terms to be described later are those that are defined in consideration of the functions in the present invention, and the definitions can differ depending on the intention or practice of users or operators. Therefore, the definitions must be considered based on the entire content of the present invention.

Further, in the preferred embodiment of the present invention to be described below, if the functional configuration of each system is already included, or have been commonly used in the technical field to which the invention pertains, in order to explain the technical components of the present invention efficiently the description thereof will be omitted. Further, the preferred embodiment is described, based on the functional configuration which must additionally be included for carrying out the present invention. Among the functional components omitted and not shown below, the functional components already used in the prior art will be easily understood by those of ordinary skill in the art. Further, the relationship between the components omitted as above and the components added for carrying out the present invention will be clearly understood by those of ordinary skill in the art.

Also, the following examples are to illustrate the important technical features of the present invention efficiently, and the terms used herein may be properly modified to so that those of ordinary skill in the art can easily understand them. However, the invention is not limited thereto.

In conclusion, the technical idea of the present invention is determined by the claims, and the following embodiments are only a means for efficiently explaining the technical idea of the present invention to those of ordinary skill in the art.

Figure 1:
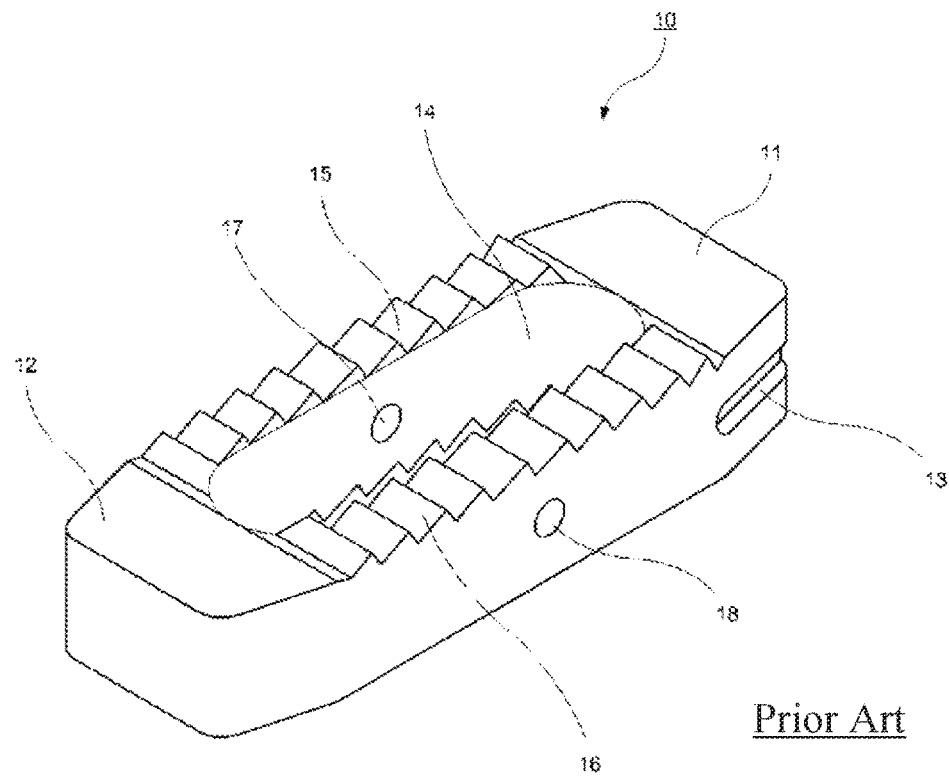
FIGS. 1 to 7 show a structure of a conventional intervertebral cage.
Figure 2:
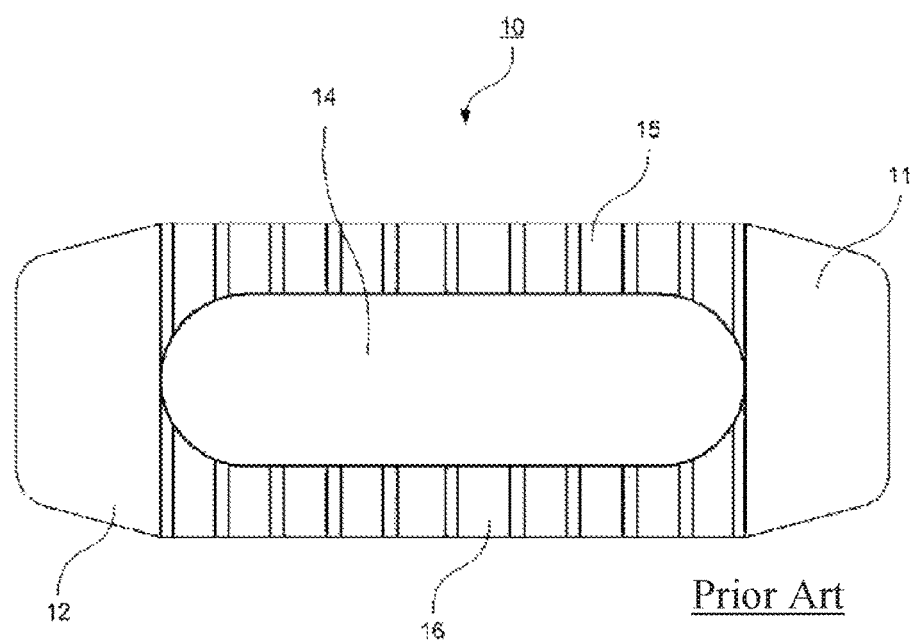
Figure 3:
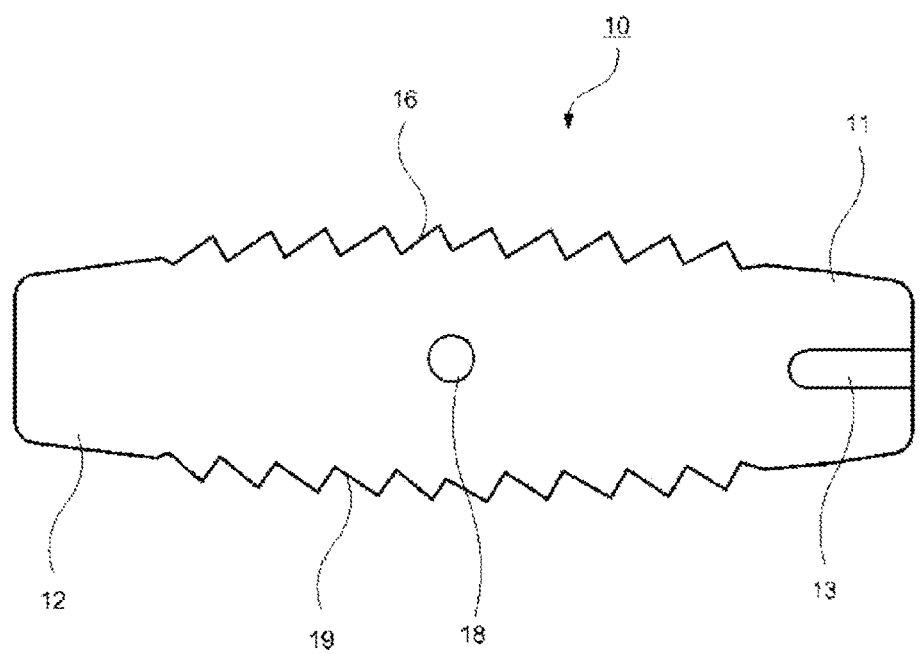
Figure 4:
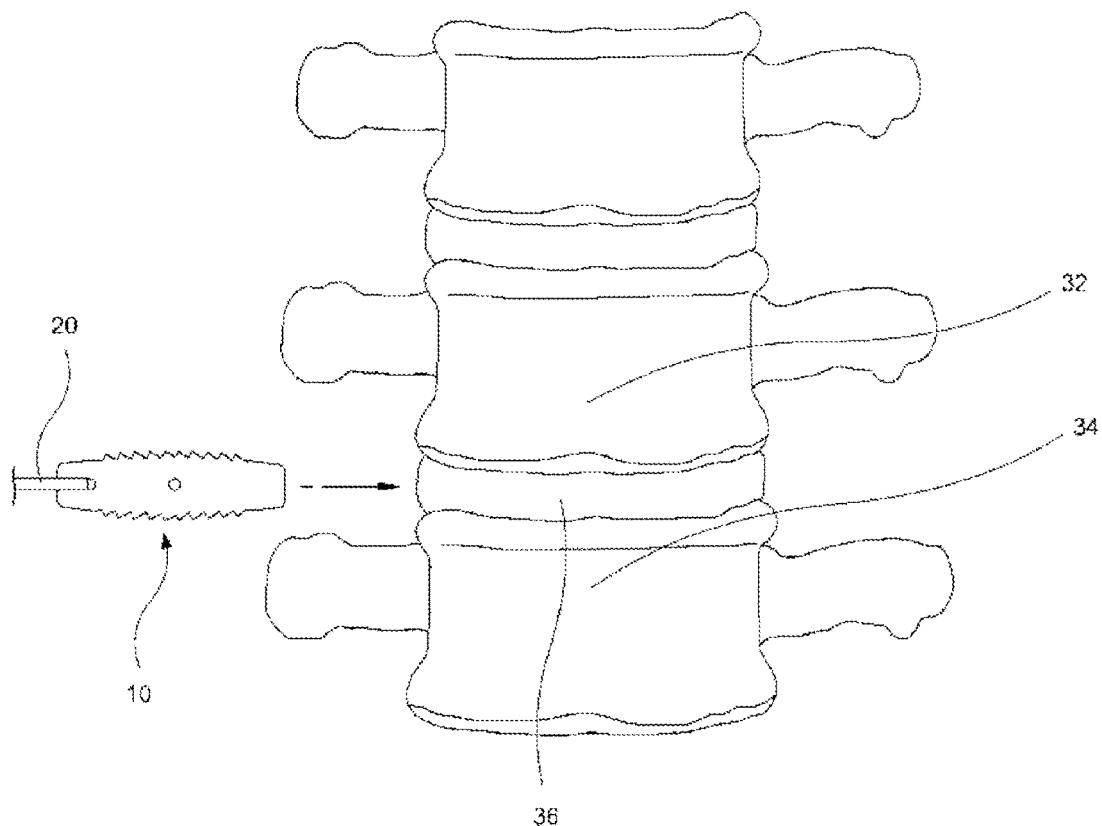
Figure 5:
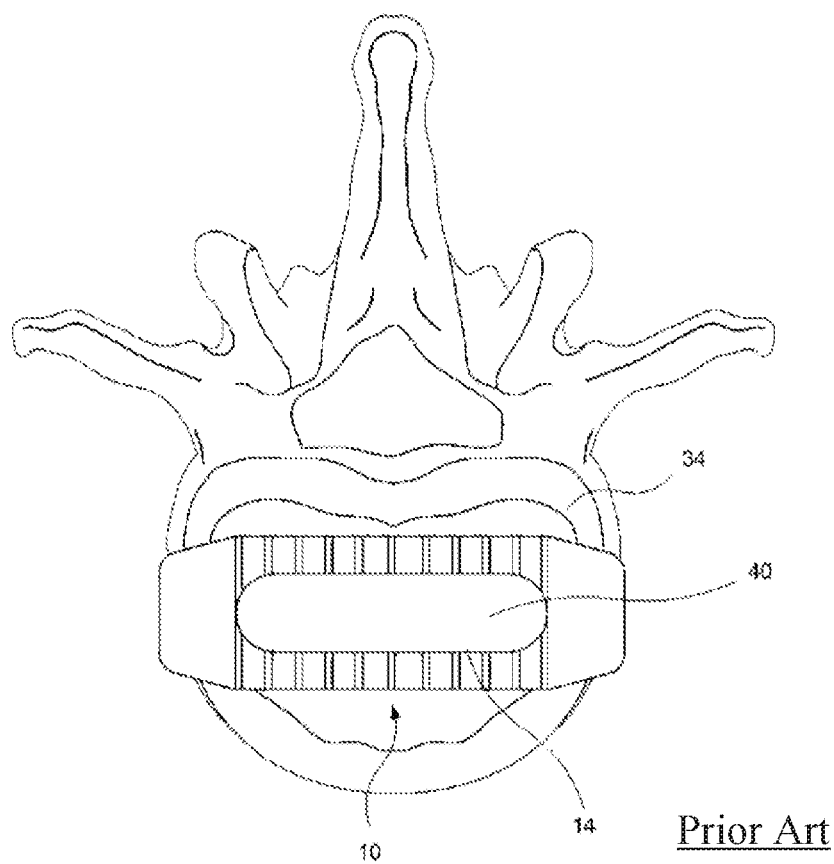
Figure 6:
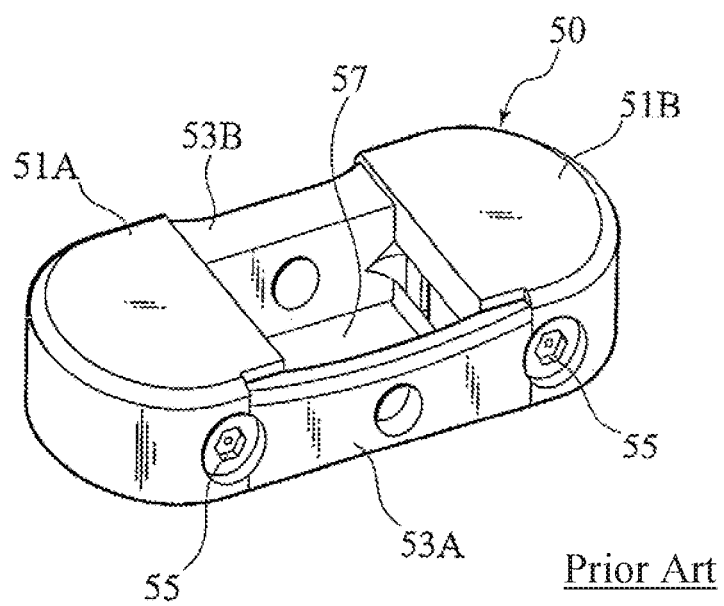
Figure 7:
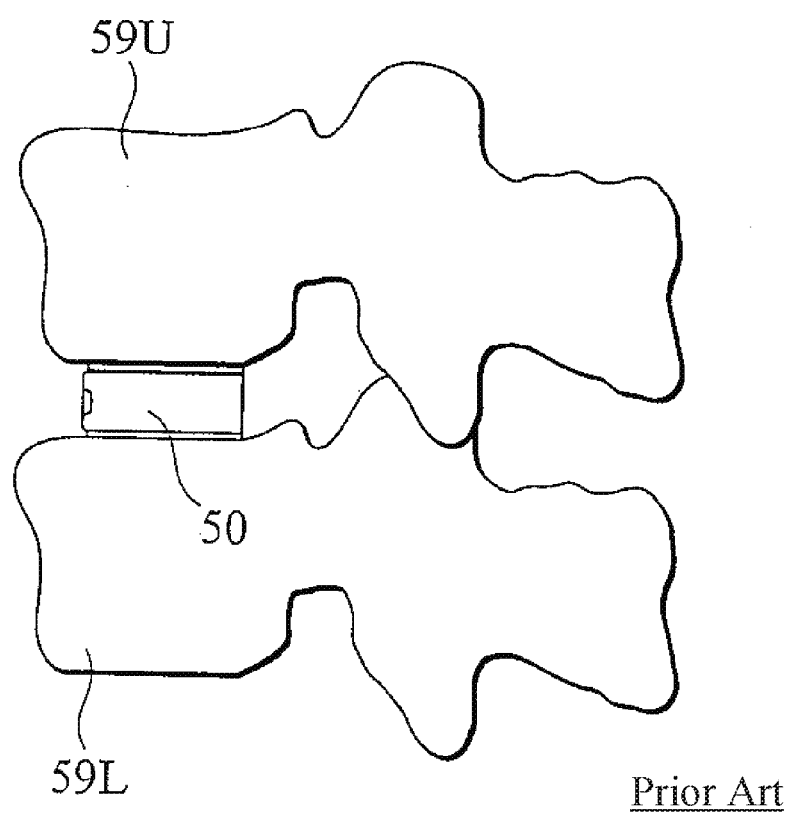
Figure 8:
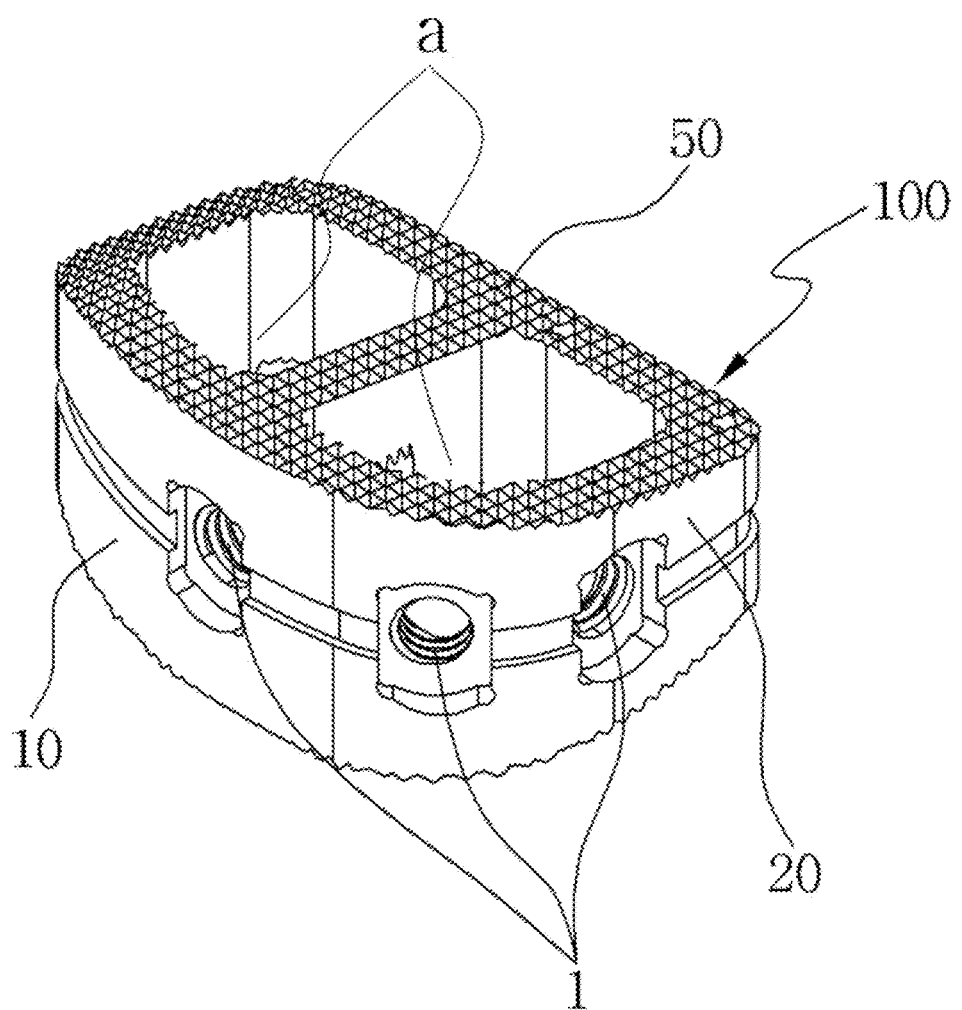
FIG. 8 is a perspective view illustrating an intervertebral cage in accordance with the present invention.
Figure 9:
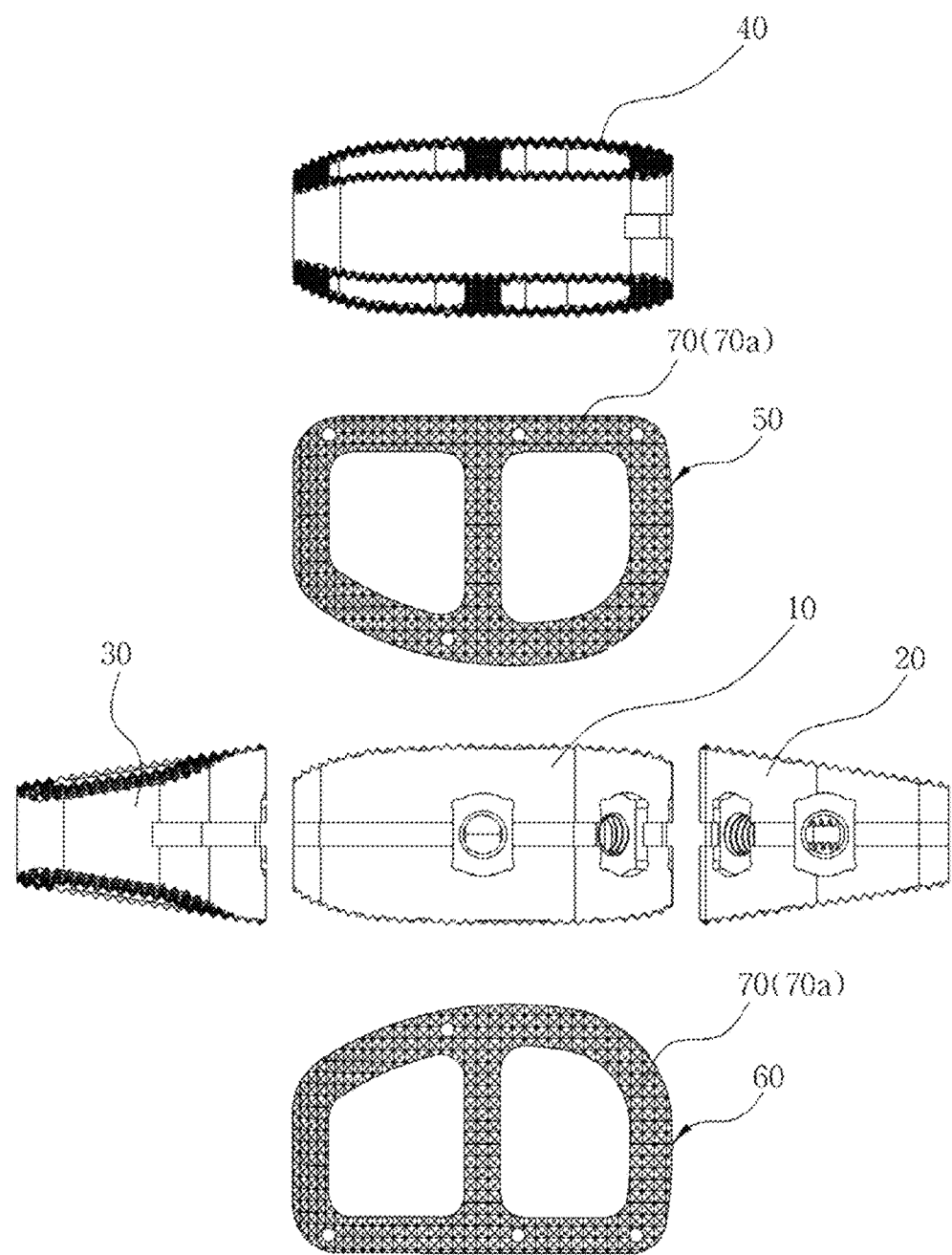
FIG. 9 shows six sides of an intervertebral cage in accordance with the present invention.

FIG. 8 is a perspective view illustrating an intervertebral cage in accordance with the present invention. FIG. 9 shows six sides of an intervertebral cage in accordance with the present invention.

As shown in FIGS. 8 and 9, the intervertebral cage 100 in accordance with the present invention has a cuboid with trapezoidal cross-section wherein the front side is thick and the rear side is thin, and the right side is thick and the left side is thin. As a result, when the intervertebral cage 100 is inserted into a spine 200 (FIG. 13), the cage can be coupled to the spines by insertion from the front side to the rear side or by the insertion in a 45-degree oblique direction from the left to the right. Also, a reversed intervertebral cage may be coupled to the spine by insertion in a 45-degree oblique direction from the right to the left. Further, the intervertebral cage of the present invention may be inserted into a lateral of the spine from the left to the right and vice-versa.

In the following, components of the present invention will be described in detail with reference to FIGS. 10 to 12.

Figure 10:
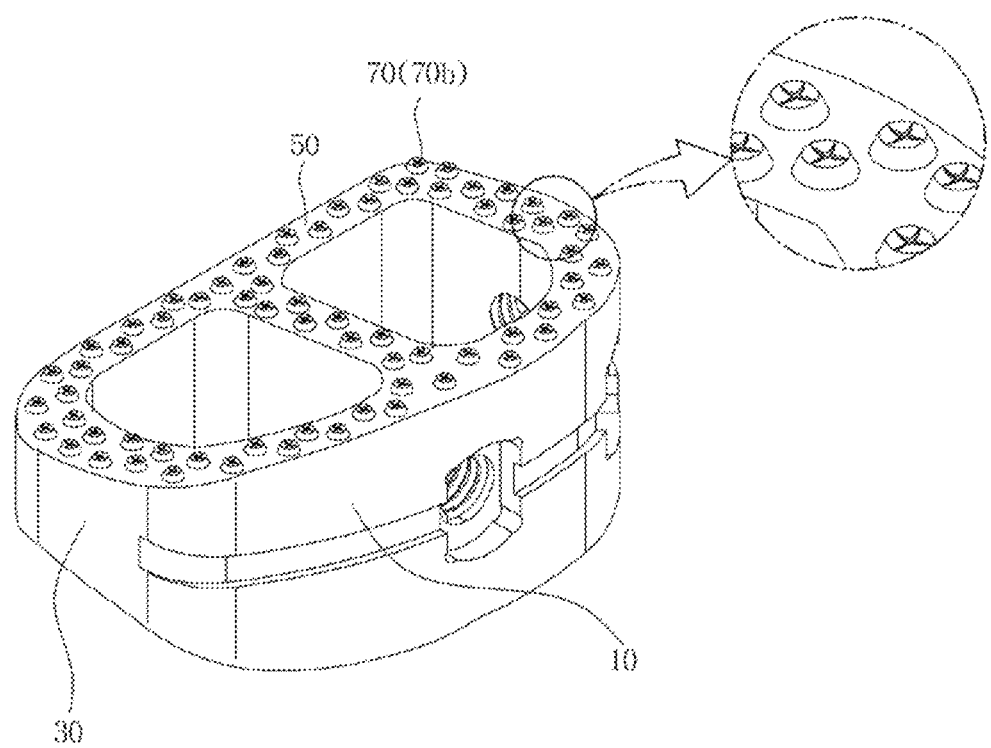
FIG. 10 is a view illustrating a slippage preventing means in accordance with a first embodiment of the present invention.

FIG. 10 is a view illustrating a slippage preventing means in accordance with a first embodiment of the present invention. FIG. 11 is a view illustrating a slippage preventing means in accordance with a second embodiment of the present invention. FIG. 12 is an enlarged view showing in detail a primary part of FIG. 11.

The intervertebral cage 100 of the present invention is a substantially cuboid configured to have a shape of "日" in which vertical holes (a) are formed on both sides.

A front side 10 of the intervertebral in accordance with the present invention has a trapezium face on the left and a rectangle face on the right.

A right lateral 20 is disposed on the right of the front side and comprises a lengthened left vertical line, a sloping upper line and lower line and a shortened right vertical line configured to form a trapezium.

A rear side 40 is disposed on the back of the front side and has a trapezium face on the left and a rectangle face on the right.

A plane 50 and a bottom 60 are disposed on the upper and lower parts of the front side and further comprises a slippage preventing means for improving a contact of vertebrae.

Also, a plurality of striking-auxiliary holes 1 for temporarily coupling and striking a tool are formed along the front side 10 and the right lateral 20 in order to allow the intervertebral cage to be inserted between the vertebrae.

Figure 11:
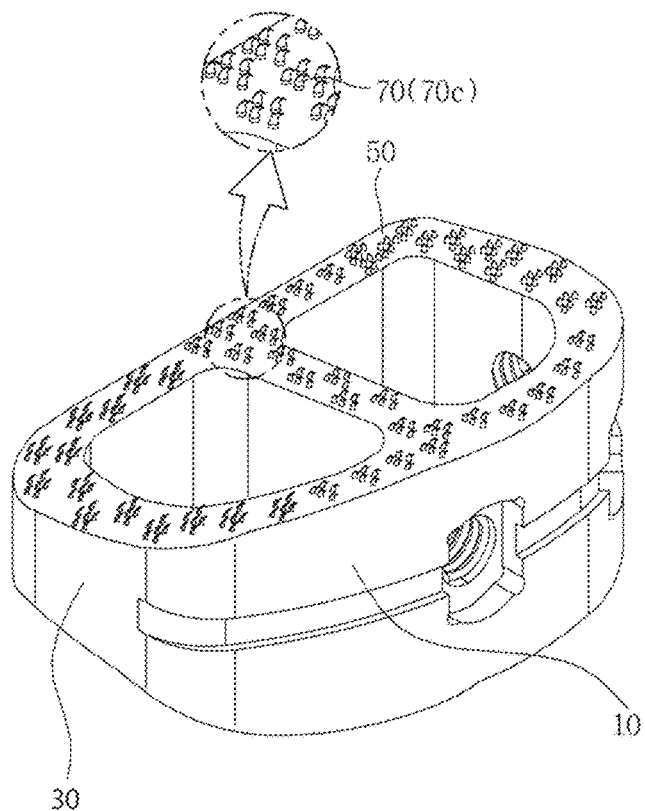
FIG. 11 is a view illustrating a slippage preventing means in accordance with a second embodiment of the present invention.

On the other hand, in one embodiment of the present invention, the slippage preventing means 70 may be configured in various patterns and may comprise an embossing structure 70a having a concave portion and a convex portion which are sequentially formed (see FIG. 9); a vacuum compressed structure 70b having a truncated cone in which the concave portion is formed on the inside so as to enable vacuum compression (see FIG. 10); and a hooked structure 70c so that it is not easily moved backward when the intervertebral cage is coupled between the vertebrae (see FIG. 11).

Figure 12:
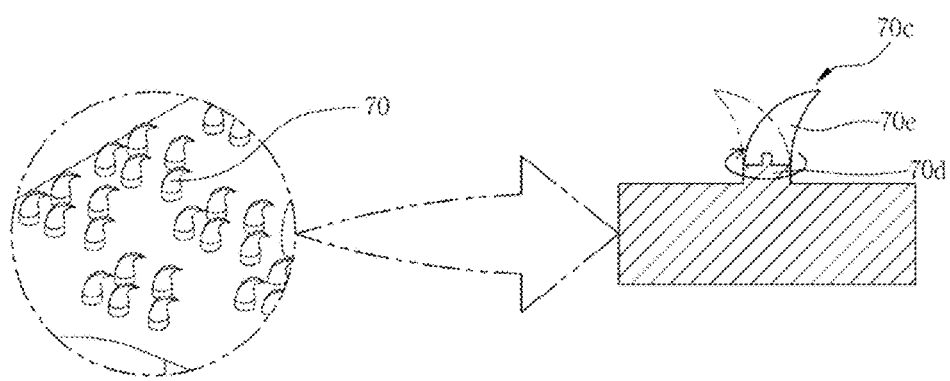
FIG. 12 is an enlarged view showing in detail a primary part of FIG. 11.

Especially, as shown in FIG. 12, the hooked structure 70c may comprise a fixing portion 70d and a movable chain hook 70e, the chain hook 70e being installed to be self-rotated. When the intervertebral cage 100 is coupled in the front side, the tip of the movable chain hook 70e may be rotated toward the direction opposite to the inserting direction and configured to not be prevented by the insertion. In contrast, when the intervertebral cage is released, the tip of the movable chain hook 70e is hooked to a flat contacting surface of the spine 200 and configured to be not easily moved. Likewise, when the intervertebral cage 100 is coupled in an oblique direction, the tip of the movable hook 70e may be obliquely arranged toward the direction opposite to the inserting direction and configured to allow the intervertebral cage to be softly inserted into the spine 200.

In contrast, when the intervertebral cage is released, the tip of the movable hook 70e is hooked to the flat contacting surface of the spine 200 and configured to be not easily moved. Also, in the case of a lateral insertion of the intervertebral cage from a rear end of the spine to a lateral direction, the tip of the movable hook 70e may be rotated toward the direction opposite to the insertion direction and configured to be softly inserted into the spine. Likewise, when the intervertebral cage is released, the tip of the movable hook 70e is hooked to the flat contacting surface of the spine 200 and configured to be not easily moved.

Figure 13:
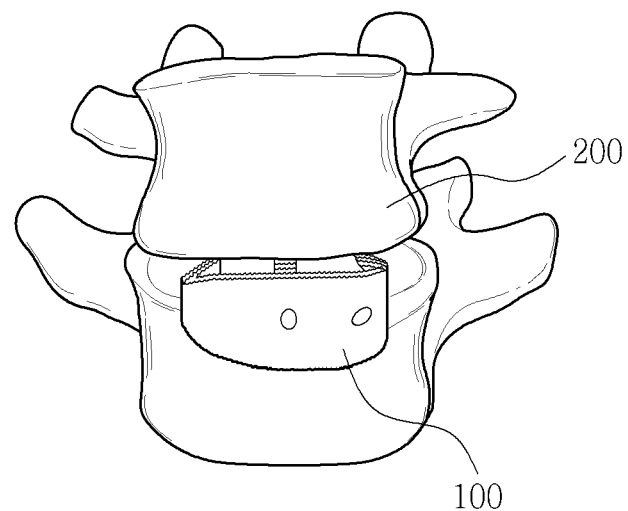
FIG. 13 is a picture showing the insertion operation of an intervertebral cage in accordance with the present invention in which the intervertebral cage has been inserted in a direction from the front side to the rear side.
Figure 14:
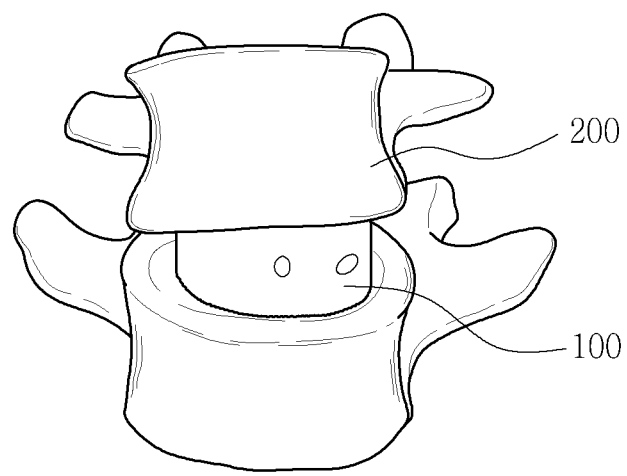
FIG. 14 is a picture showing the inserted state of the intervertebral cage in which the intervertebral cage has been inserted in a direction from the front side to the rear side.
Figure 15:
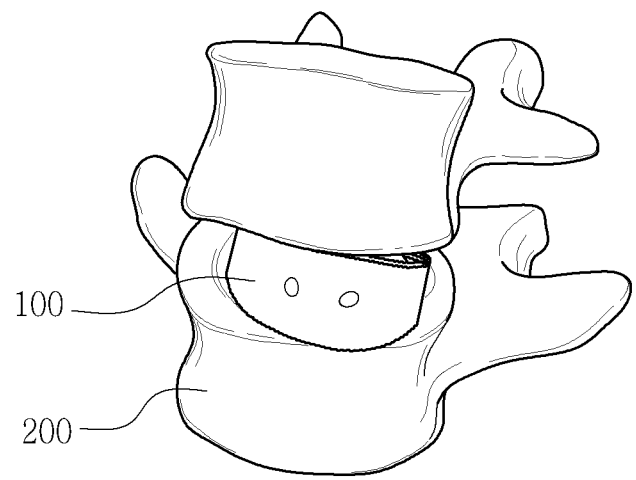
FIG. 15 is a picture showing the insertion operation of an intervertebral cage in accordance with the present invention in which the intervertebral cage has been inserted in the diagonal direction.
Figure 16:
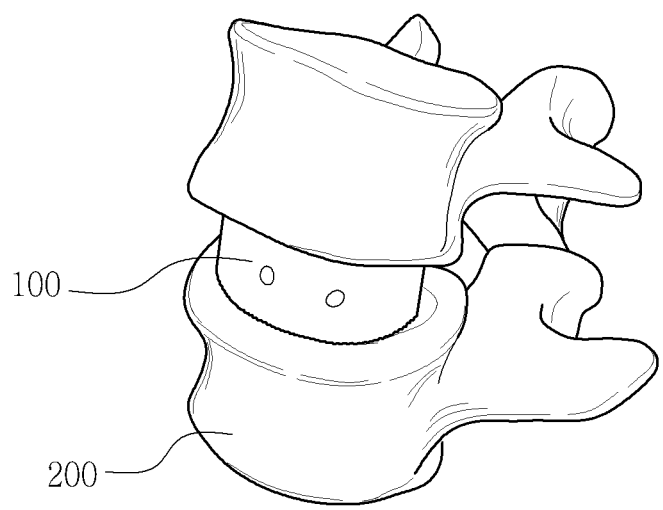
FIG. 16 is a picture showing the inserted state of the intervertebral cage in accordance with the present invention in which the intervertebral cage has been inserted in the diagonal direction.
Figure 17:
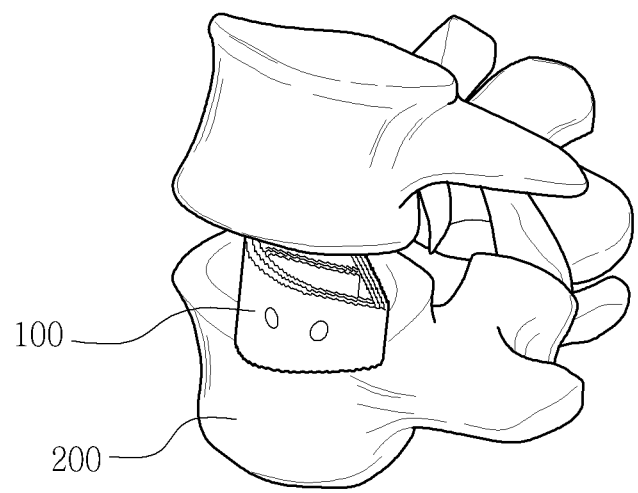
FIG. 17 is a picture showing the insertion operation of an intervertebral cage in accordance with the present invention in which the intervertebral cage has been inserted from the side.
Figure 18:
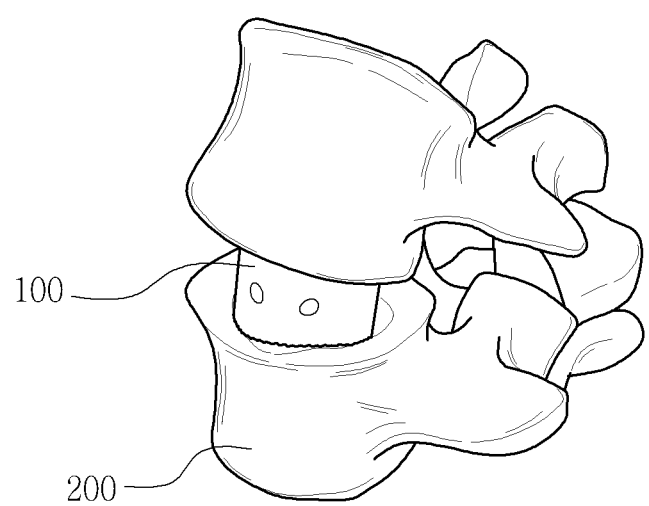
FIG. 18 is a picture showing the inserted state of the intervertebral cage in accordance with the present invention in which the intervertebral cage has been inserted from the side.
Figure 19:
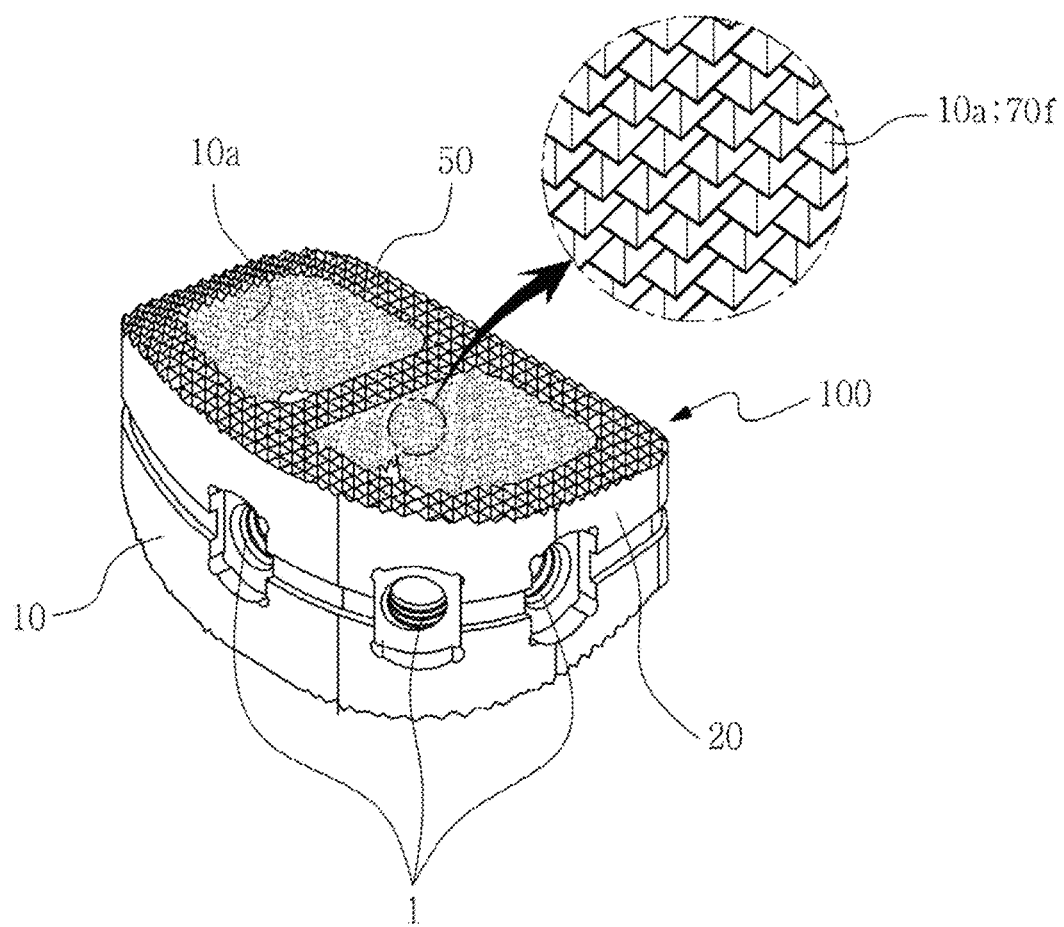
FIG. 19 is a perspective view showing a slippage preventing means which has been formed in an inner lateral of an intervertebral cage in accordance with the present invention.

In the following, an assembling method of the intervertebral cage in accordance with the present invention will be described in detail with reference to FIGS. 13 to 19 as follows:

FIG. 13 is a picture showing the insertion operation of an intervertebral cage in accordance with the present invention in which the cage has been inserted in a direction from the front side to the rear side. FIG. 14 is a picture showing the inserted state of the intervertebral cage in which the cage has been inserted in a direction of from a front side to a rear side. FIG. 15 is a picture showing the insertion operation of an intervertebral cage in accordance with the present invention in which the intervertebral cage has been inserted in the diagonal direction. FIG. 16 is a picture showing the inserted state of the intervertebral cage in accordance with the present invention in which the intervertebral cage has been inserted in the diagonal direction. FIG. 17 is a picture showing the insertion operation of an intervertebral cage in accordance with the present invention in which the intervertebral cage has been inserted from the side. FIG. 18 is a picture showing the inserted state of the intervertebral cage in accordance with the present invention in which the intervertebral cage has been inserted from the side.

The intervertebral cage 100 of the present invention may be inserted and coupled to the spine 200 through a front side and an inclined plane of the spine or from a rear side of the spine to a left direction and a right direction. The intervertebral cage 100 may have a form in which a front side and a left lateral are high and a rear side and a right lateral are low and have a shape of "H" in which two vertical holes (a) are formed.

Accordingly, a connecting portion between a left lateral and a rear may be formed at the thinnest section, while a connection portion between the front and the right lateral may be formed at the thickest section. As a result, when the intervertebral cage 100 is coupled to the spine 200 in an oblique direction, the intervertebral cage may be easily inserted and coupled to a left oblique surface by means of the insertion from the thinner portion to the thicker portion. In case of a reversed intervertebral cage about a horizontal axis, since the left and right laterals are reversed, the reversed intervertebral cage may be easily inserted and coupled.

When the intervertebral cage 100 is coupled to the spine 200 in an oblique direction, the intervertebral cage 100 may be easily coupled with the spine by knocking the cage with a tool through a plurality of strike aids holes 1 positioned in the corner direction. Also, when the intervertebral cage 100 is inserted from the frontal direction to a rear direction, since the front is thick and the rear is thin, the intervertebral cage may be easily inserted and coupled. Likewise, when the intervertebral cage 100 is inserted from the frontal direction, the intervertebral cage may be easily coupled with the spine 200 by knocking the cage with the tool through the plurality of striking-auxiliary holes 1 positioned in the front Also, when the intervertebral cage 100 is coupled with the spine 200 from the rear side 40 to the left lateral, since the left lateral 30 is thin and the right lateral 20 is thick, the intervertebral cage 100 may be easily coupled with the spine 200 from the rear side 40 to the left lateral. It is of course possible that, when the intervertebral cage 100 is inserted and coupled in the right lateral, the intervertebral cage 100 may be reversed about a horizontal axis. Also, when the intervertebral cage 100 is coupled in a left lateral direction, the intervertebral cage 100 may be easily coupled with the spine 200 by knocking the cage with a tool through a plurality of strike aids holes 1 positioned in the right lateral 20.

Hereinafter, an operating method of the intervertebral cage in accordance with the present invention will be described in detail as follows:

The intervertebral cage 100 of the present invention may have a shape of "□" in which two vertical holes (a) are formed, a connecting portion between the left lateral 30 and the rear side 40 being formed at the thinnest section, while a connection portion between the front side 10 and the right lateral 20 being formed at the thickest section.

When the intervertebral cage 100 of the present invention is inserted and coupled to the spine, because the thickness of the front side 10 of the intervertebral cage is high, while that of the rear side 40 thereof is low, the intervertebral cage 100 may be inserted from the frontal direction to the rear direction of the spine 200. Further, because the thickness of the left lateral 30 is low, while that of the right lateral 20 is high, the intervertebral cage 100 may be inserted from the left lateral direction to the right lateral direction of the spine 200. Also, because the connecting portion between the left lateral 30 and the rear side 40 of the intervertebral cage 100 is formed at the thin section, while the connection portion between the front side 10 and the right lateral 20 thereof is formed at the thick section, the intervertebral cage 100 may be inserted from the right oblique direction to the left oblique direction of the spine 200. It is of course possible that, when the intervertebral cage 100 is reversed about a horizontal axis, the intervertebral cage may be inserted from the left lateral oblique direction to the right lateral oblique direction or from the right lateral oblique direction to the left lateral oblique direction. Also, the intervertebral cage may not slip when the intervertebral cage 100 of the present invention is coupled to the spine 200 by further including a slippage preventing means 70 formed in an upper portion and a lower portion of the intervertebral cage.

That is, the slippage preventing means 70 may be formed between the spines 200 in order to prevent the possibility that the intervertebral cage 100 coupled between the spines 200 could be separated by slippage. The slippage preventing means 70 may selectively comprise an embossing structure 70a having a concave portion and a convex portion, the concave and the convex portions being formed in order, a vacuum compressed structure 70b having a truncated cone in which a concave portion is formed on inside so as to vacuum compressed, or a hooked structure 70c to not be easily moved backward when the cage is coupled between the vertebrae. As a result, the intervertebral cage 100 of the present invention may be easily coupled without slipping between the spines 200 during the coupling of the intervertebral cage.

Further, the embossing structure 70f having a concave portion and a convex portion, the concave and the convex portions being sequentially formed, may be formed at an inner lateral 10a of the intervertebral cage 100. Both insides of the embossing structure 70f are hollow, into which space an autograft or an allograft is inserted so as to advantageously achieve a bony fusion. Accordingly, the intervertebral cage of the present invention inserted to the spines may not separate from the spines by the autograft or the allograft positioned insides of the embossing structure so as to effectively achieve the bony fusion.

According to the present invention, when the intervertebral cage 100 is coupled with the spine 200 in an oblique direction, the intervertebral cage may be easily inserted and coupled to the left oblique surface.

As described above, according to an intervertebral cage in accordance with various embodiments of the present invention, the intervertebral cage may be inserted in every face, i.e., a front side, a lateral side and an inclined plane of a spine and configured such that it is possible to freely select the inserting direction of intervertebral cage in accordance with the needs of a user. This results in a maximization of the advantages of such operation.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An intervertebral cage for spinal implants, the intervertebral cage comprising:
   a front side;
   a right lateral side;
   a left lateral side;
   a rear side;
   a top side; and
   a bottom side,
   wherein the intervertebral cage is substantially cuboid with trapezoidal cross-section, the front side being thicker than the rear side, the right lateral side being thicker than the left lateral side, a thickness of the intervertebral cage decreasing along an anterior-posterior axis with a vertical dimension of the front side being a largest and a vertical dimension of the rear side being a smallest,
   wherein cross-sections of the intervertebral cage perpendicular to the anterior-posterior axis comprise a slanting portion and a flat portion of a predetermined length in the to side and the bottom side,
   wherein at least one of the top side and the bottom side has a slippage preventing structure formed thereon,
   wherein the slippage preventing structure includes a hooked structure, and
   wherein the hooked structure comprises a fixing portion and a movable hook, the movable hook being configured to self-rotate in accordance with an orientation of insertion of the intervertebral cage between vertebrae.

2. The intervertebral cage of claim 1, wherein a plurality of striking-auxiliary holes are formed along the front side and the right lateral side in order to allow the intervertebral cage to be inserted between vertebrae.

3. The intervertebral cage of claim 1, wherein the intervertebral cage has an inner space defined therein, wherein an embossing structure is formed on an inner side surface of the intervertebral cage.

* * * * *